United States Patent
Konstandopoulos et al.

(10) Patent No.: US 8,141,413 B2
(45) Date of Patent: Mar. 27, 2012

(54) PARTICULATE MATTER CONCENTRATION MEASURING APPARATUS

(75) Inventors: Athanasios G. Konstandopoulos, Thessaloniki (GR); Fumishige Miyata, Gifu (JP); Takafumi Kasuga, Gifu (JP); Yasuhiro Ishii, Gifu (JP)

(73) Assignees: Ibiden Co., Ltd., Ogaki-Shi (JP); Athanasios G. Konstandopoulos, Thessaloniki (GR)

( * ) Notice: Subject to any disclaimer, the term of this patent is extended or adjusted under 35 U.S.C. 154(b) by 140 days.

(21) Appl. No.: 12/694,291

(22) Filed: Jan. 27, 2010

(65) Prior Publication Data
US 2010/0242457 A1 Sep. 30, 2010

(30) Foreign Application Priority Data
Mar. 31, 2009 (JP) .................... PCT/JP2009/056746

(51) Int. Cl.
G01M 15/10 (2006.01)
(52) U.S. Cl. .................................. 73/114.71; 73/23.31
(58) Field of Classification Search ............... 73/114.71, 73/114.75, 114.76, 23.31
See application file for complete search history.

(56) References Cited

U.S. PATENT DOCUMENTS

| | | | |
|---|---|---|---|
| 7,472,610 B2 * | 1/2009 | Clerc et al. ................. | 73/862.52 |
| 7,658,064 B2 * | 2/2010 | Konstandopoulos ........... | 60/297 |
| 7,866,146 B2 * | 1/2011 | Konstandopoulos ........... | 60/311 |
| 7,891,176 B2 * | 2/2011 | Konstandopoulos ........... | 60/297 |
| 2007/0163445 A1 | 7/2007 | Sakashita et al. | |
| 2008/0087007 A1 * | 4/2008 | Konstandopoulos ........... | 60/286 |
| 2008/0087012 A1 | 4/2008 | Konstandopoulos | |
| 2008/0134796 A1 * | 6/2008 | Clerc et al. ...................... | 73/756 |
| 2010/0242455 A1 * | 9/2010 | Konstandopoulos et al. .. | 60/311 |
| 2010/0242457 A1 * | 9/2010 | Konstandopoulos et al. .. | 60/311 |
| 2010/0242463 A1 * | 9/2010 | Konstandopoulos et al. .. | 60/324 |
| 2011/0061368 A1 * | 3/2011 | Miyata et al. ................... | 60/277 |
| 2011/0072789 A1 * | 3/2011 | Konstandopoulos et al. .. | 60/276 |

FOREIGN PATENT DOCUMENTS

| | | |
|---|---|---|
| EP | 1916394 | 4/2008 |
| JP | 2002-285822 | 10/2002 |
| JP | 2005-172652 | 6/2005 |
| JP | 2008-101603 | 4/2008 |
| JP | 2008-284538 | 11/2008 |

OTHER PUBLICATIONS

Deguch et al. Clarification on Characteristics of Pressure Drop and Behavior of Fine Particles Loading on Porous Filter Collection of Lecture Notes (2): Mechanical Engineering Contress, 2006 Japan (MECJ-06), Sep. 15, 2006, pp. 283-284 Japan Society of Mechanical Engineers, Japan.

* cited by examiner

*Primary Examiner* — Freddie Kirkland, III
(74) *Attorney, Agent, or Firm* — Ditthavong Mori & Steiner, P.C.

(57) ABSTRACT

A particulate matter concentration measuring apparatus is configured to measure a concentration of particulate matter in exhaust gas flowing through an exhaust line of a diesel engine. The apparatus includes an exhaust gas extraction line diverging from the exhaust line and having a flow passage cross-sectional area smaller than a flow passage cross-sectional area of the exhaust line. A particulate matter detection filter has a cell wall and is provided in the exhaust gas extraction line. A flow velocity of the exhaust gas passing through the cell wall is more than or equal to approximately 0.02 m/s and less than or equal to approximately 2.0 m/s. A differential pressure sensing part is configured to sense a differential pressure generated between an inlet and an outlet of the particulate matter detection filter.

9 Claims, 12 Drawing Sheets

US 8,141,413 B2

PARTICULATE MATTER CONCENTRATION MEASURING APPARATUS

CROSS-REFERENCE TO RELATED APPLICATION

The present application is based on and claims the benefit of priority of PCT International Application No. PCT/JP2009/056746, filed on Mar. 31, 2009, the entire contents of which are incorporated herein by reference.

BACKGROUND OF THE INVENTION

1. Field of the Invention

The present invention relates to a particulate matter concentration measuring apparatus configured to measure a concentration of particulate matter (PM) in exhaust gas.

2. Description of the Related Art

FIG. 1 of European Patent Application Publication No. EP 1916394 A1 discloses an apparatus 20PM (PM Sensor) which is known as a conventional apparatus for detecting a concentration of particulate matter primarily of C (carbon) in exhaust gas from diesel engines. This particulate matter concentration measuring apparatus 20PM includes a secondary exhaust line 21A diverging from an exhaust line 21, a particulate matter detection filter 22A provided in the secondary exhaust line 21A, and a differential pressure measuring part 22B that measures a differential pressure ΔP caused between the inlet and outlet of the particulate matter detection filter 22A. Further, a flow rate measuring part 24 and a temperature measuring part T1 are provided in the secondary exhaust line 21A, and a heater 22H is provided in the particulate matter detection filter 22A.

In the conventional particulate matter concentration measuring apparatus 20PM according to European Patent Application Publication No. EP 1916394 A1, the differential pressure ΔP across the particulate matter detection filter 22A, the temperature T of exhaust gas in the secondary exhaust line 21A, and the flow rate Q2 of the exhaust gas in the secondary exhaust line 21A are measured. The mass of the particulate matter trapped with the particulate matter detection filter 22A per unit time, PM [g/h], is calculated from the measured differential pressure ΔP, exhaust gas temperature T, and exhaust gas flow rate Q2. The concentration of the particulate matter in the exhaust gas, PMconc [g/m$^3$], is calculated from this mass of the particulate matter, PM [g/h].

Further, European Patent Application Publication No. EP 1916394 A1 describes a diesel particulate filter (DPF) 22 formed of porous ceramic and provided in the exhaust line 21 as part of a conventional exhaust gas purifying apparatus 20. The secondary exhaust line 21A of the conventional particulate matter concentration measuring apparatus 20PM is connected to the upstream side of the diesel particulate filter 22 in the flow of the exhaust gas. The mass of the particulate matter flowing into the diesel particulate filter 22, PMenter full filter [g/h], is calculated from the determined concentration of the particulate matter in the exhaust gas, PMconc [g/m$^3$], and the engine operating condition or the flow rate of gas flowing into the diesel particulate filter 22 in the exhaust line 21, Q1.

The entire contents of European Patent Application Publication No. EP 1916394 A1 are incorporated herein by reference.

SUMMARY OF THE INVENTION

According to an aspect of the present invention, a particulate matter concentration measuring apparatus is configured to measure a concentration of particulate matter in exhaust gas flowing through an exhaust line of a diesel engine. The apparatus includes an exhaust gas extraction line, a particulate matter detection filter, and a differential pressure sensing part. The exhaust gas extraction line diverges from the exhaust line and has a flow passage cross-sectional area smaller than a flow passage cross-sectional area of the exhaust line. The particulate matter detection filter has a cell wall and is provided in the exhaust gas extraction line. A flow velocity of the exhaust gas passing through the cell wall is more than or equal to approximately 0.02 m/s and less than or equal to approximately 2.0 m/s. The differential pressure sensing part is configured to sense a differential pressure generated between an inlet and an outlet of the particulate matter detection filter.

BRIEF DESCRIPTION OF THE, DRAWINGS

Other objects, features and advantages of the present invention will become more apparent from the following detailed description when read in conjunction with the accompanying drawings, in which.

DETAILED DESCRIPTION OF THE PREFERRED EMBODIMENTS

First Embodiment

Figure 2:
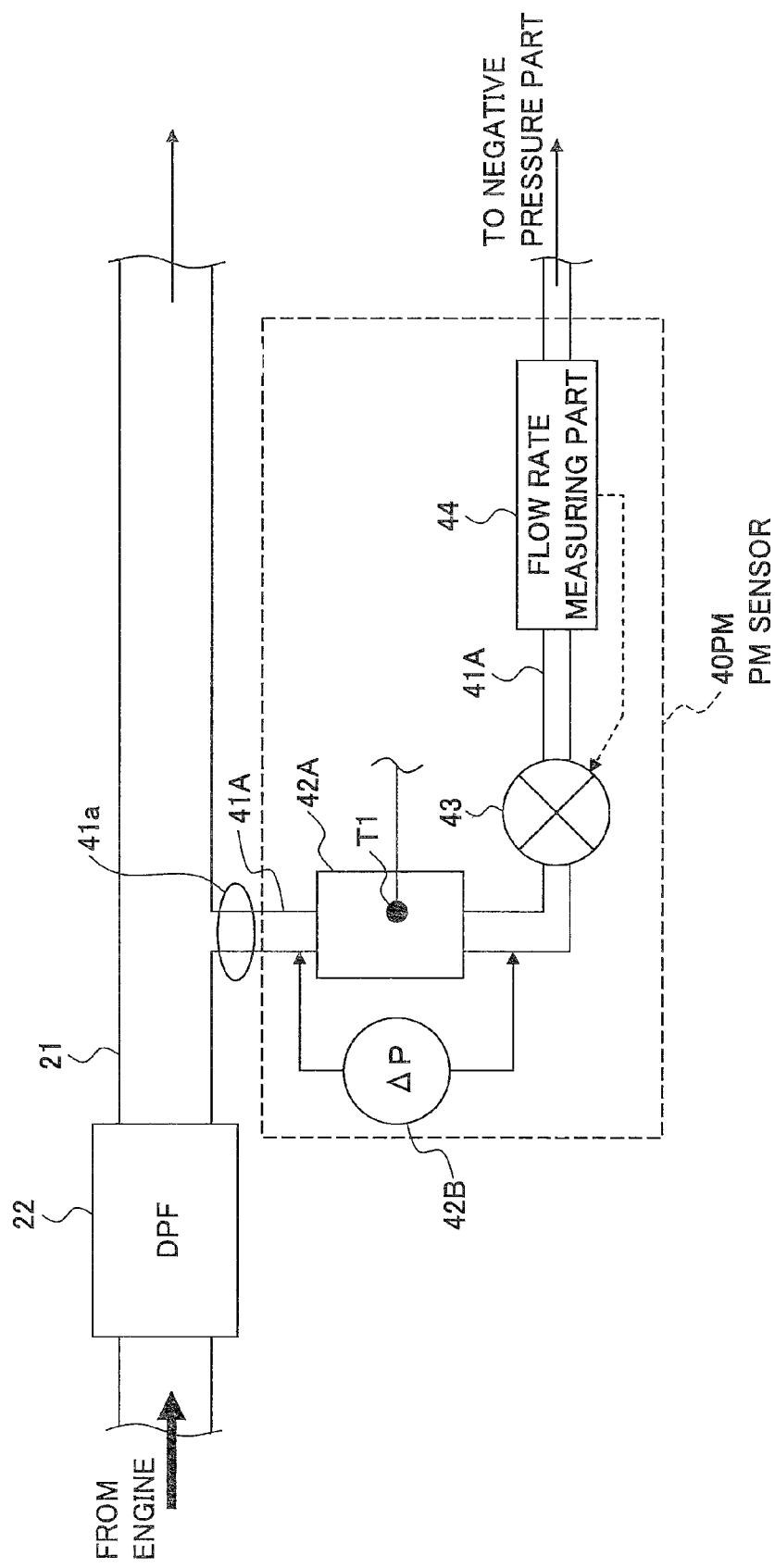
FIG. 2 is a diagram illustrating a particulate matter concentration measuring apparatus according to a first embodiment of the present invention.

FIG. 2 illustrates a particulate matter concentration measuring apparatus 40PM (PM sensor) according to a first embodiment of the present invention. In FIG. 2, the parts described above are referred to by the same reference numerals, and a description thereof is omitted. In the case where an abnormality occurs in the diesel particulate filter (DPF) 22 so that the leakage of particulate matter into the exhaust line 21 is more than or equal to the downstream-side threshold of the diesel particulate filter (DPF) 22, the particulate matter concentration measuring apparatus 40PM of FIG. 2 may be used to detect this and to give the ala/m or cause a lamp to flash or turn on.

Referring to the first embodiment of the present invention in FIG. 2, an exhaust gas extraction line 41A having an exhaust gas extraction part 41a at one end is connected through the exhaust gas extracting part 41a to the exhaust line 21 of a diesel engine, in which the diesel particulate filter (DPF) 22 is formed, on the downstream side of the diesel particulate filter (DPF) 22. A particulate matter detection filter 42A illustrated in FIG. 3, a flow rate control valve 43, and a flow rate measuring part 44 for measuring the flow rate Q2 of the exhaust gas extraction line 41A are connected in series to the exhaust gas extraction line 41A. The exhaust gas extraction line 41A has its downstream end connected to a part lower in pressure than the inlet of the particulate matter detection filter 41A, such as a pressure tank or an air intake part, so that exhaust gas in the exhaust line 21 is suctioned to the particulate matter detection filter 42A. This is the same as connecting a suction pump to the downstream end of the exhaust gas extraction line 41A. As a result, it is possible to ensure the feeding of exhaust gas to the particulate matter detection filter 42A.

Further, the temperature measuring part T1 that measures the temperature of the particulate matter detection filter 42A is provided in the particulate matter detection filter 42A. Further, a differential pressure measuring part (differential pressure sensing part) 42B is provided to measure (sense) the differential pressure ΔP across the particulate matter detection filter 42A. The exhaust gas extraction part 41a is smaller in flow passage cross-sectional area than the exhaust line 21. The flow rate control valve 43 is controlled by the flow rate measuring part 44 so that the flow rate of exhaust gas flowing through the exhaust gas extraction line 41A is controlled to a predetermined value.

Diaphragm pressure gauges or other known pressure gauges such as gauge-type, bellows, and thermal pressure gauges may be used as the above-described differential pressure measuring part 42B. Further, known flowmeters such as hot wire flowmeters and Venturi flowmeters may be used as the flow rate measuring part 44.

Figure 3:
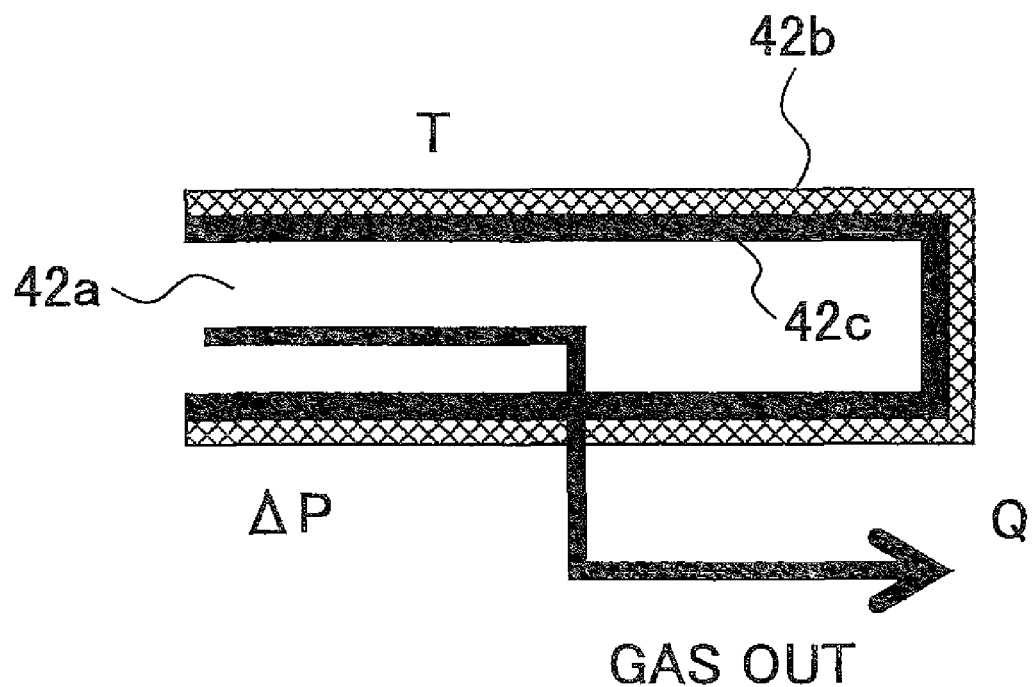
FIG. 3 is a diagram for illustrating the function of a particulate matter detection filter in the particulate matter concentration measuring apparatus according to the first embodiment of the present invention.

FIG. 3 illustrates an example of the particulate matter detection filter 42A according to the first embodiment of the present invention. In the example of FIG. 3, only a single cell 42b is formed in the particulate matter detection filter 42A. However, the particulate matter detection filter 42A may be fanned of multiple cells 42b. Further, the particulate matter detection filter 42A may be a plate-shaped filter.

According to this embodiment of the present invention, the particulate matter detection filter 42A includes one or more gas passages 42a, which, as a whole, have a volume of less than or equal to approximately 5%, for example, approximately 0.05% to approximately 5%, of the total volume of exhaust gas passages in the diesel particulate filter (DPF) 22 or less than or equal to approximately 65 ml, for example, approximately 0.05 ml to approximately 65 ml, or have a filtration area of approximately 0.1 cm² to approximately 1000 cm² (preferably, a filtration area of approximately 1 cm² to approximately 10 cm²). For example, the gas passages 42a are formed to be rectangular in cross-sectional shape or are closed at one end (closed at the rear end in FIG. 3).

Referring to the first embodiment of the present invention in FIG. 3, each cell 42b, formed of porous ceramic, forms the corresponding gas passage 42a, which is open at one end and closed at another end. The exhaust gas introduced into the gas passage 42a moves to an adjacent gas passage through its cell wall of porous ceramic, when particulate matter is trapped on the inner wall surface of the cell 42b to form a particulate matter layer 42c.

Figure 4:
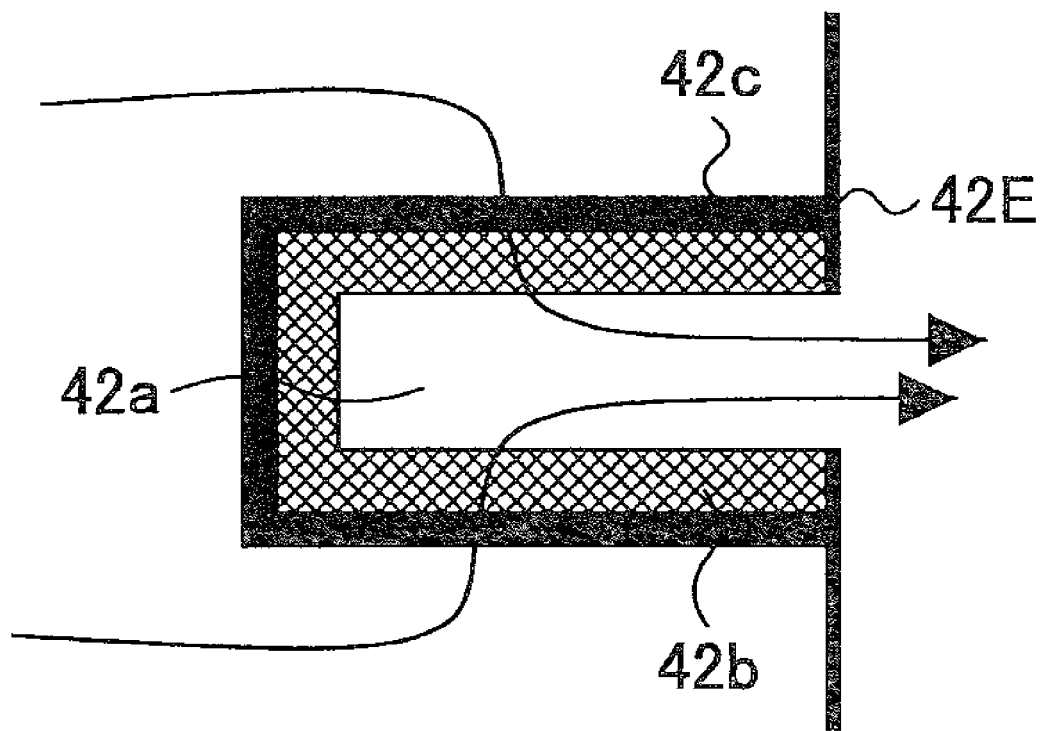
FIG. 4 is a diagram illustrating a variation of the particulate matter detection filter in the particulate matter concentration measuring apparatus according to the first embodiment of the present invention.

FIG. 4 illustrates a variation of the cell 42b of FIG. 3 according to the first embodiment of the present invention. In the cell 42b of FIG. 4, exhaust gas flows from outside the cell 42b to the gas passage 42a inside the cell 42b through its cell wall, when the particulate matter layer 42c is deposited on the outer surface of the cell 42b.

Figure 1:
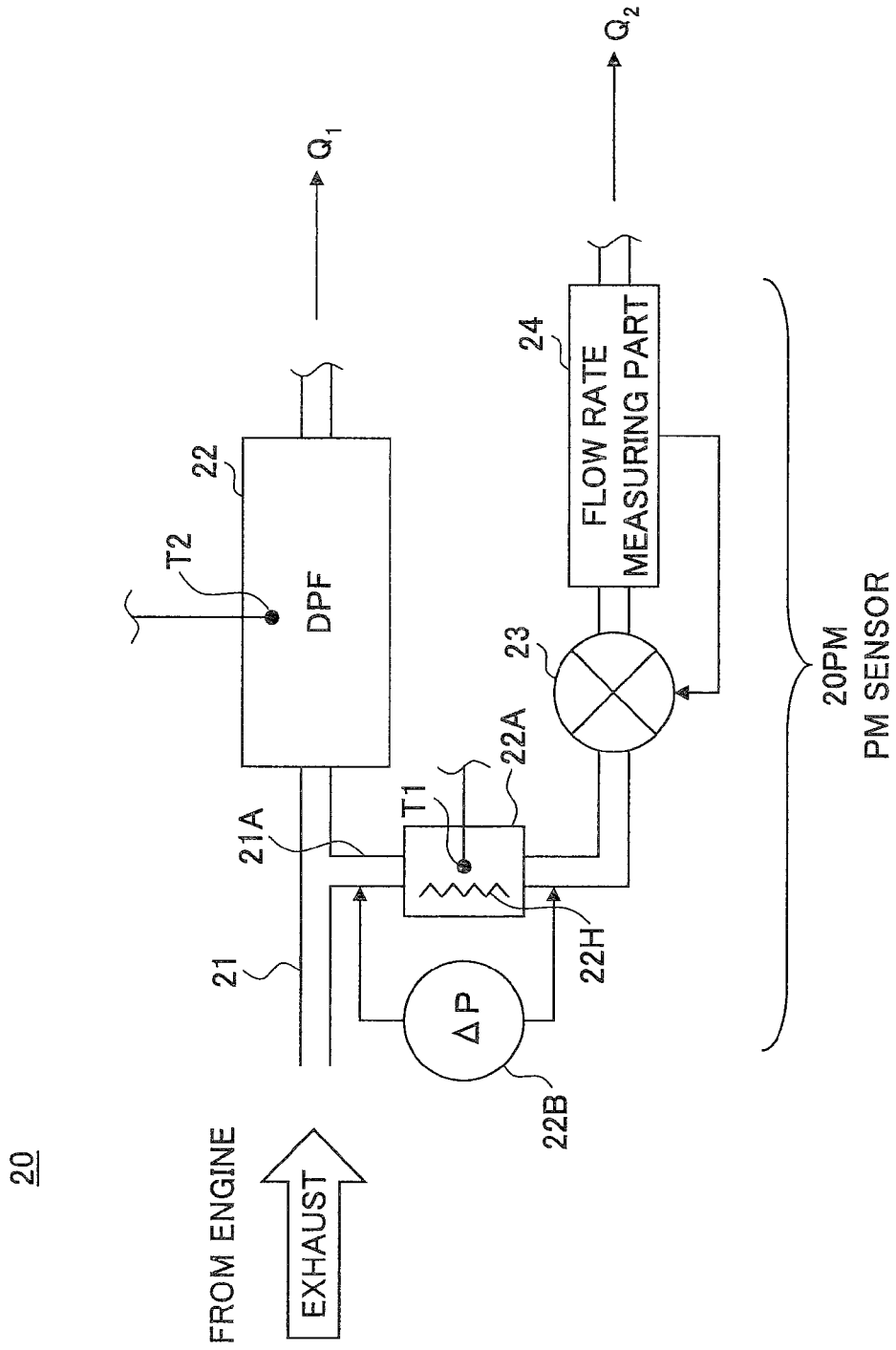
FIG. 1 is a diagram illustrating a conventional exhaust gas purifying apparatus.

Similar cells are also formed in the diesel particulate filter (DPF) 22 in the conventional exhaust gas purifying apparatus 20 illustrated in FIG. 1. However, the external shapes of the gas passages 42a and the cells 42b do not necessarily have to be substantially equal in size or cross-sectional shape to the gas passages in the diesel particulate filter (DPF) 22, and may be any shape such as a substantially circular shape, a substantially quadrangular shape, a substantially octagonal shape, or a substantially elliptic shape. Further, the porous ceramic of the particulate matter detection filter 42A (cell 42b) does not have to be substantially equal in material quality to the porous ceramic of the diesel particulate filter (DPF) 22. The particulate matter detection filter 42A is not limited in material to ceramic. The gas passages 42a are formed to have a total volume of less than or equal to approximately 5% of the total volume of exhaust gas passages in the diesel particulate filter (DPF) 22 or less than or equal to approximately 65 ml, or have a filtration area of approximately 0.1 cm² to approximately 1000 cm² (preferably, a filtration area of approximately 1 cm² to approximately 10 cm²). This causes uniform deposition of a particulate matter layer on the cell 42b. As a result, it is possible to measure the amount of particulate matter deposited in the diesel particulate filter (DPF) 22 with simplicity and accuracy as described below. The particulate matter detection filter 42A may also be provided with its bottom part on the upstream side in the flow of the exhaust gas as illustrated in the first embodiment of the present invention in FIG. 4.

In the particulate matter concentration measuring apparatus 40PM of FIG. 2 according to the first embodiment of the present invention, the amount of accumulation of particulate matter trapped in the particulate matter detection filter 42A is calculated by the following equation:

$$\Delta P = \frac{\mu Q}{2 V trap}(\alpha + Ws)^2 \left[ \frac{Ws}{Kw\alpha} + \frac{1}{2Ksoot} \ln\left(\frac{\alpha}{\alpha - 2W}\right) + \frac{4FL^2}{3}\left(\frac{1}{(\alpha - 2W)^4} + \frac{1}{\alpha^4}\right) \right] + \quad (1)$$

$$\frac{\rho Q^2 (\alpha + Ws)^4}{V trap^2} \left[ \frac{\beta Ws}{4} + 2\zeta \left[\frac{L}{\alpha}\right]^2 \right],$$

where "ΔP" represents a differential pressure expressed in the unit of [Pa], "μ" represents a kinetic viscosity coefficient expressed in the unit of [Pa·S], "Q" represents the flow rate of exhaust gas expressed in the unit of [m³/h], "α" represents the length of one side of a cell expressed in the unit of [m], "ρ" represents the density of exhaust gas expressed in the unit of [g/m³], "Vtrap" represents filter volume expressed in the unit of [m³], "Ws" represents wall thickness expressed in the unit of [m], "Kw" represents the gas permeability of a wall expressed in the unit of [m$^{-1}$], "Ksoot" represents the gas permeability of a trapped particulate material layer expressed in the unit of [m$^{-1}$], "W" represents the thickness of the trapped particulate material layer expressed in the unit of [m], "F" represents a coefficient (=28.454), "L" represents effective filter length expressed in the unit of [m], "β" represents the Forchheimer coefficient of a porous wall expressed in the unit of [m$^{-1}$], and "ζ" represents a differential pressure due to passage through the filter expressed in the unit of [Pa].

Next, the mass of the particulate matter trapped in the particulate matter detection filter 42A (cell 42b), "msoot," is determined by the following equation:

$$W = \frac{\alpha - \sqrt{\alpha^2 - \frac{msoot}{Ncells \times L \times \rho soot}}}{2}, \quad (2)$$

where "msoot" is the mass [g] of the trapped particulate matter, "Ncells" is the number of openings of cells on the inlet side, and "ρsoot" is the density of the trapped particulate matter.

Then, the trapped amount per unit time "PM" [g/s] is determined by dividing "msoot" by the time [s] that has passed since the last regeneration of the particulate matter detection filter 42A.

Once the mass of the particulate matter deposited per unit time, "PM" [g/s], is thus determined, the concentration of the particulate matter in the exhaust gas, "PMconc" [g/m³], is determined, using the flow rate of exhaust gas passing through the particulate matter detection filter 22A, "Q2" [m³/s], by:

$$PM [g/s] = PMconc [g/m^3] \times Q2 [m^3/s], \quad (3)$$

According to this embodiment, in the case where an abnormality occurs in the diesel particulate filter (DPF) 22 so that the leakage of particulate matter into the exhaust line 21 is more than or equal to the downstream-side threshold of the diesel particulate filter (DPF) 22, it is possible to detect such an abnormality and to give the alarm or cause a lamp to flash or turn on by providing this particulate matter concentration measuring apparatus 40PM on the downstream side of the diesel particulate filter (DPF) 22 as illustrated in FIG. 2.

In a diesel engine system having such an exhaust gas purifying apparatus, the particulate matter concentration measuring apparatus 40PM is desired to have high measurement accuracy in order to immediately detect an abnormality caused in the diesel particulate filter 22.

Figure 5:
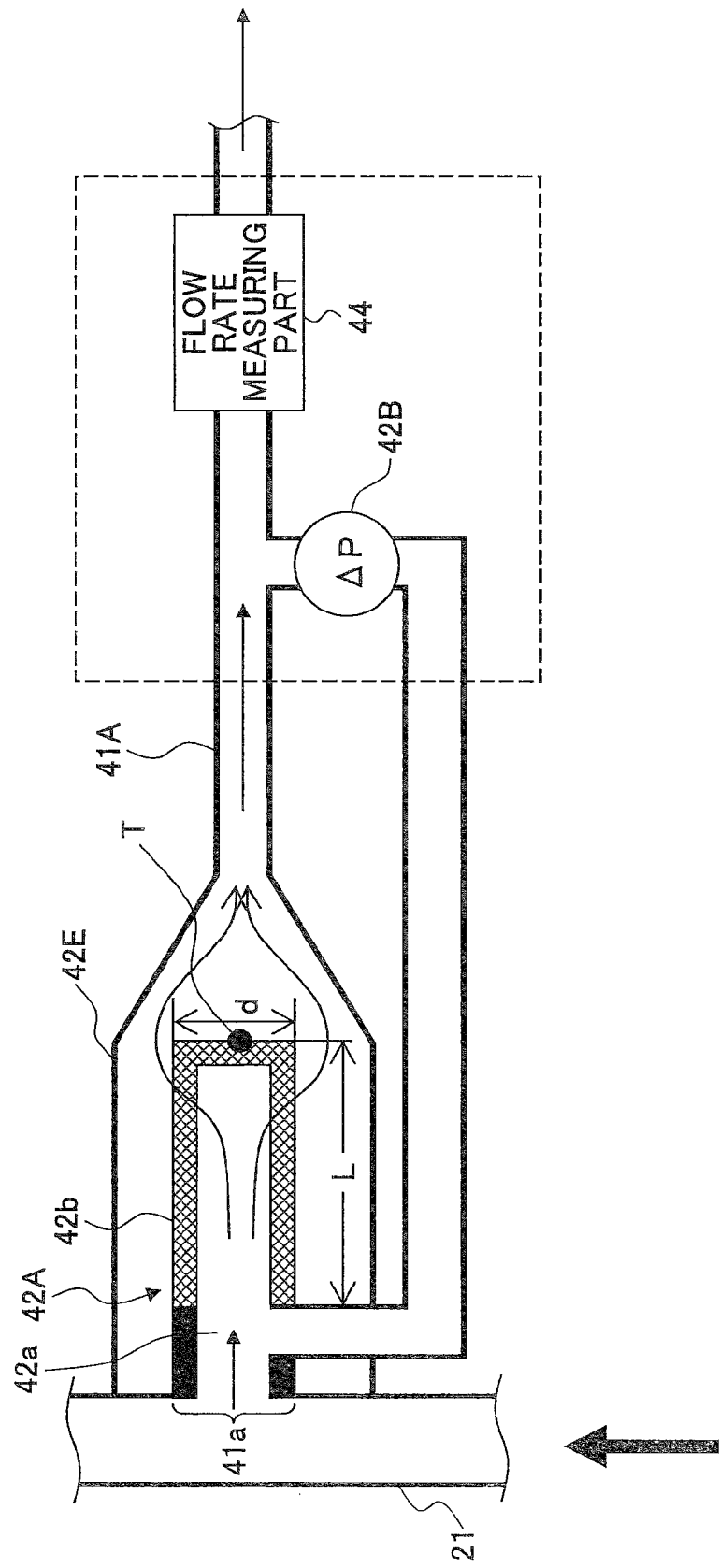
FIG. 5 is a diagram illustrating a more detailed configuration of the particulate matter concentration measuring apparatus according to the first embodiment of the present invention.

Referring to FIG. 5, the particulate matter detection filter 42A according to the first embodiment of the present invention has its one end forming the exhaust gas extraction part 41a, and is housed in a housing 42E connected to the exhaust gas extraction line 41A. The differential pressure measuring part 42B, which may be a diaphragm pressure gauge, is formed on the downstream side of the particulate matter detection filter 42A. The differential pressure measuring part 42B has one end connected to the upstream end of the particulate matter detection filter 42A and has the other end connected to the exhaust gas extraction line 41A on the downstream side of the particulate matter detection filter 42A. This allows the differential pressure measuring part 42B to measure the differential pressure across the cell 42b forming the particulate matter detection filter 42A.

Figure 6:
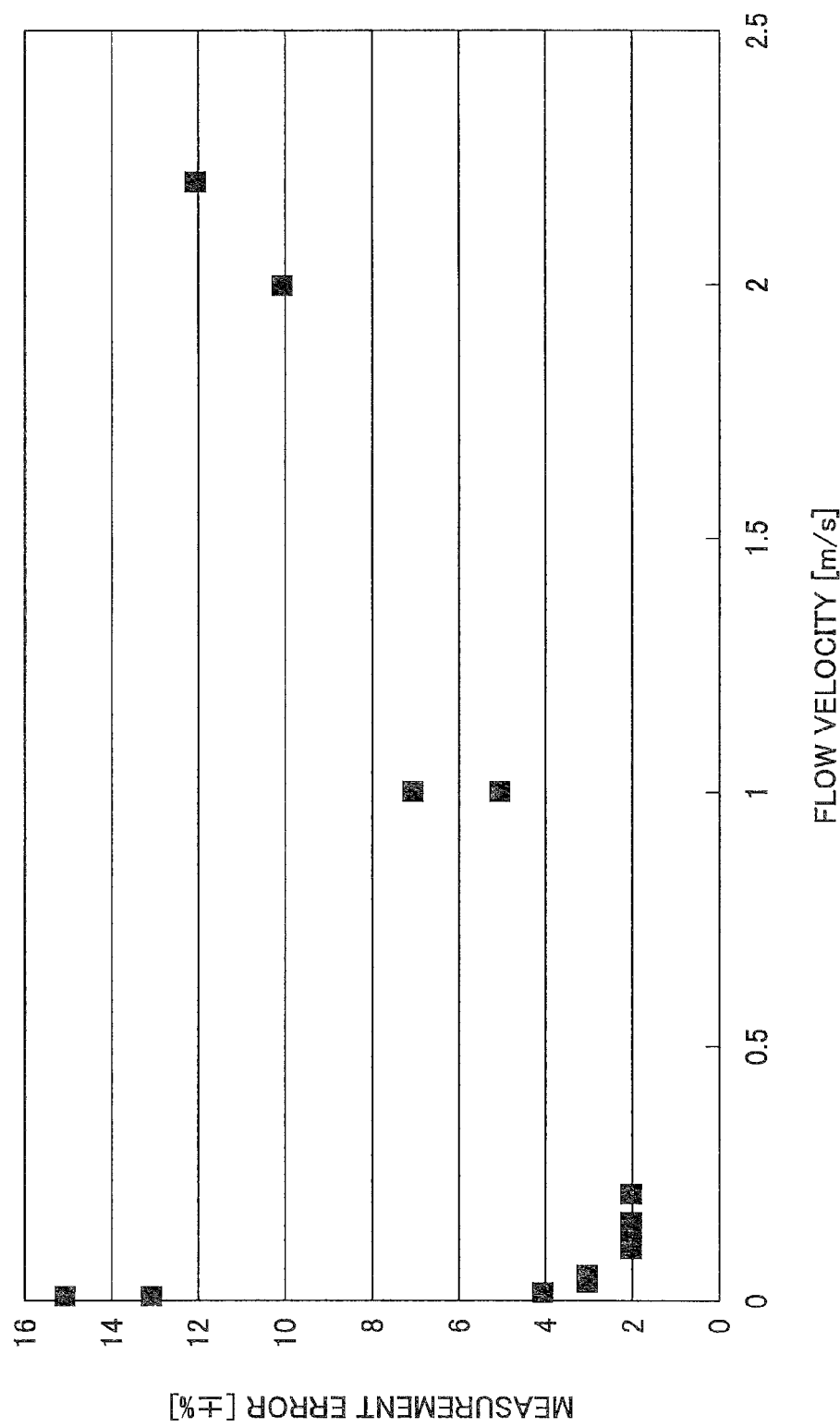
FIG. 6 is a graph illustrating the relationship between the flow velocity of exhaust gas passing through a cell wall and measurement error in the particulate matter concentration measuring apparatus according to the first embodiment of the present invention.

FIG. 6 shows the relationship between the measurement error between the particulate matter concentration in exhaust gas determined in accordance with Eq. (1) through Eq. (3) and the actual measurement (true value, described below) of particulate matter in the exhaust line 21 and the flow velocity of the exhaust gas at the time of passing through the cell wall of the cell 42b according to the first embodiment of the present invention.

Figure 7A:
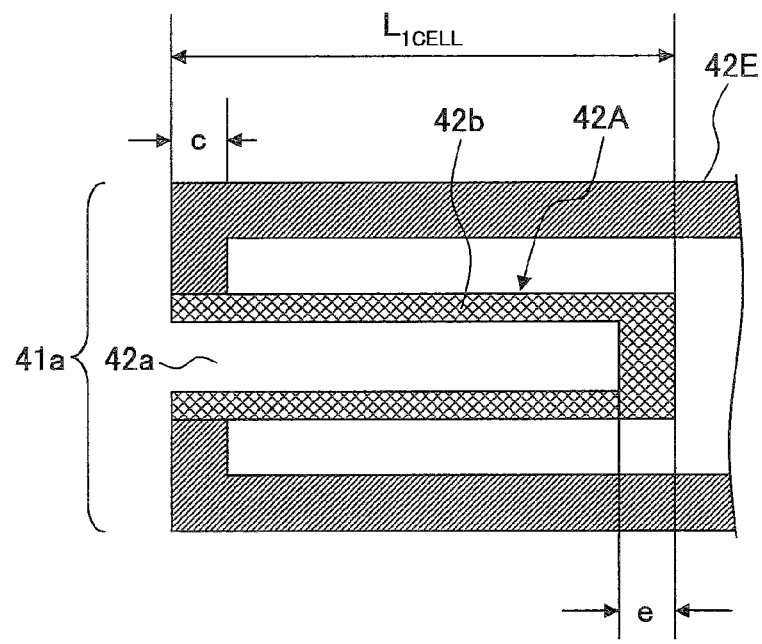
FIGS. 7A through 7C are diagrams illustrating the details of the experiment of FIG. 6 according to the first embodiment of the present invention.
Figure 7B:
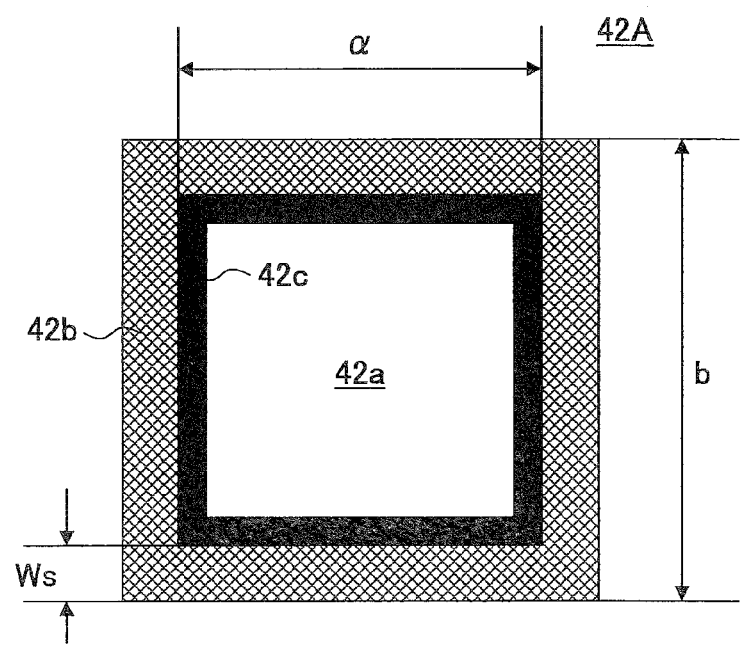

The experiment of FIG. 6 was conducted by driving a diesel engine twice at a rotational speed of 2000 rpm and a torque of 40 Nm, twice at a rotational speed of 2500 rpm and a torque of 40 Nm, twice at a rotational speed of 3000 rpm and a torque of 40 Nm, and twice at a rotational speed of 3500 rpm and a torque of 40 Nm with respect to Samples A through E shown in Table 1, having the shape illustrated in the first embodiment of the present invention in FIGS. 7A and 7B.

Referring to FIGS. 7A and 7B, the particulate matter detection filter 42A has its one end forming the exhaust gas extraction part 41a, and includes the cell 42b forming the gas passage 42a. Particulate matter is trapped on the inner wall surface of the cell 42b, forming the particulate matter layer 42c. In FIGS. 7A and 7B, "L1cell" represents the length of the cell 42b, "c" represents the thickness of a wall portion of the housing 42E that holds the cell 42b on its entrance side, "e" represents the thickness of the bottom of the cell 42b, "α" represents the length of one (interior) side of the cell 42b, "b" represents the length of one side of the particulate matter detection filter 42A (the length of one exterior side of the cell 42b), and "Ws" represents the wall thickness of the cell 42b. "L1cell" minus "c" defines the effective filter length of the particulate matter detection filter 42A.

TABLE 1

|  | A | B | C | D | E |
|---|---|---|---|---|---|
| α | 3.38 mm | 3.38 mm | 3.38 mm | 3 × 3 A CELLS PERIPHERAL COATING | 3.38 mm |
| ws | 0.4 mm | 0.4 mm | 0.4 mm | ☐■☐ | 0.4 mm |
| c | 1.0 mm | 2.0 mm | 1.0 mm |  | 1.0 mm |
| e | 0.5 mm | 1.0 mm | 0.5 mm | ■☐■ | 0.5 mm |
| L1cell | 15.0 mm | 30.0 mm | 15.0 mm | ☐■☐ | 8.5 mm |
| POROSITY | 40% | 40% | 60% | — | 25% |

Figure 7C:
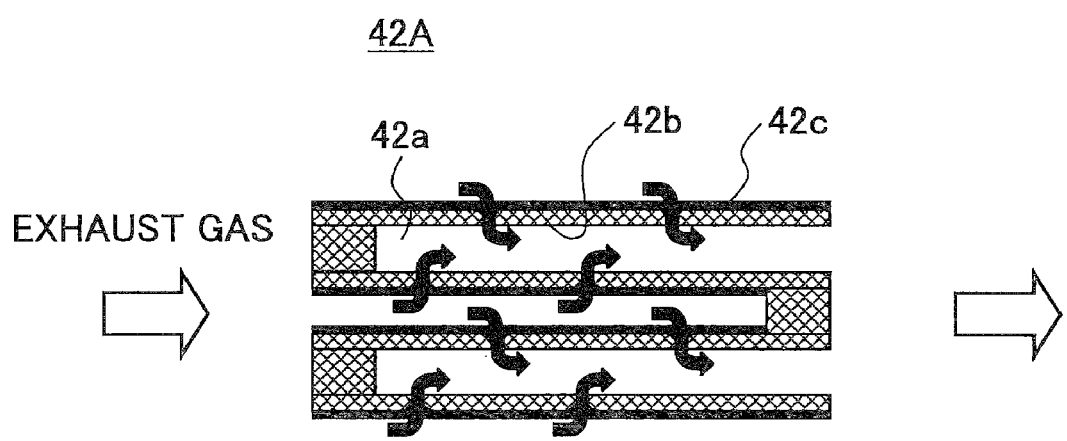

In Table 1, Sample D is a peripherally-sealed aggregate of cells of Sample A in a 3 by 3 matrix structure, where the cells formed are closed at alternate ends as illustrated in FIG. 7C. In Table 1, white squares and black squares indicate open cells and closed cells, respectively, in this cell aggregate in a view from the upstream side, for example.

The exhaust gas in the exhaust line 21 is filtered and the actual measurement of trapped particulate matter (described below) is determined as a true value in the configuration of FIG. 2 according to the first embodiment of the present invention. A deviation of the amount of particulate matter determined by Eq. (1) through Eq. (3) from this true value is determined as the measurement error.

Figure 8:
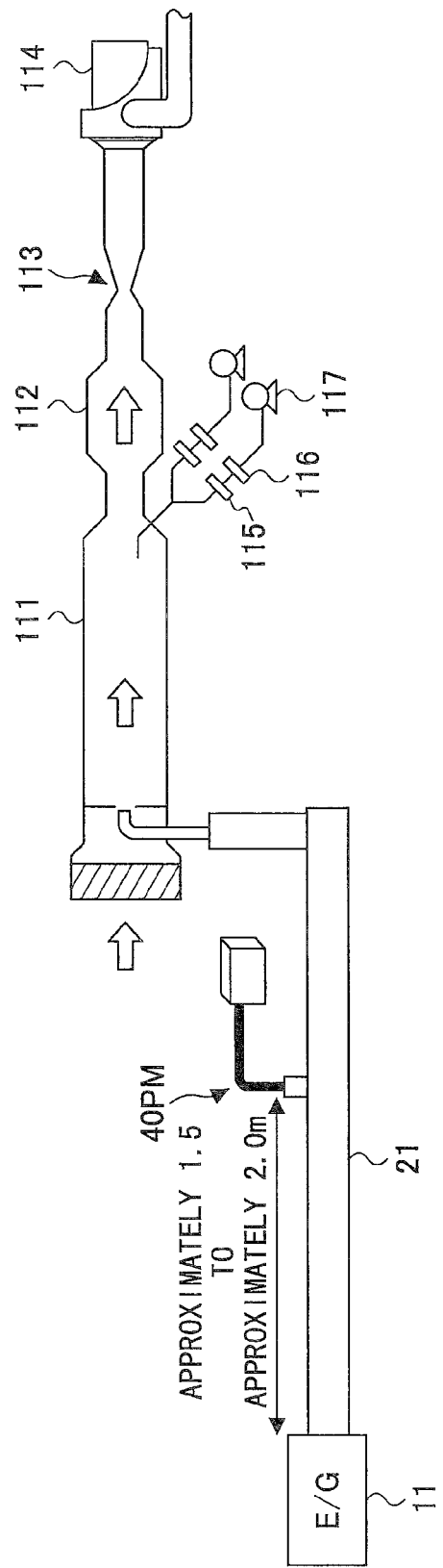
FIG. 8 is a diagram illustrating a configuration for measuring the true value of the amount of particulate matter in the experiment of FIG. 6 according to the first embodiment of the present invention.

As illustrated in the first embodiment of the present invention in FIG. 8, the exhaust gas discharged into the exhaust line 21 from a diesel engine (E/G) 11 is guided to a dilution tunnel 111 where clean air is introduced, and is diluted and cooled to a temperature of approximately 52° C. or less. Then, the exhaust gas is collected on a primary collection filter 115 and a secondary collection filter 116, and its mass is measured with a microbalance. Thereby, the amount of particulate matter in the exhaust gas is actually measured directly, and is converted to concentration in the exhaust line 21 to be determined as a true value. The measurement error is determined by comparing the value (PMconc) calculated by the particulate matter concentration measuring apparatus 40PM provided (at a distance of approximately 1.5 m through approximately 2.0 m from the diesel engine 11) to the same exhaust line 21 with the true value. In the configuration of FIG. 8 according to the first embodiment of the present invention, after passing through the dilution tunnel 111, the exhaust gas is suctioned by a blower 114 through a heat exchanger 112 and a critical flow Venturi tube 113. Further, a blower 117 is also provided on the downstream side of the primary collection filter 115 and the secondary collection filter 116 to suction the exhaust gas.

Referring to the graph of FIG. 6 illustrating the relationship between the flow velocity of exhaust gas passing through a cell wall and measurement error according to the first embodiment of the present invention, the measurement error tends to increase as the flow velocity of exhaust gas passing through the cell wall of the cell 42b increases. This is believed to show that particulate matter in the cell 42b is prone to be deposited unevenly as the flow rate of exhaust gas in the cell 42b increases.

On the other hand, the graph of FIG. 6 according to the first embodiment of the present invention shows that the measurement error is minimized at a flow velocity of approximately 0.1 m/s and increases again if the flow velocity is lower than that.

Table 2 shows the details of the experiment of FIG. 6 according to the first embodiment of the present invention.

TABLE 2

| | FILTER | INTAKE FLOW RATE [l/min] | FLOW VELOCITY [m/s] | MEASUREMENT ERROR [±%] |
|---|---|---|---|---|
| EXAMPLE 1 | A | 0.6 | 0.13 | 2 |
| EXAMPLE 2 | A | 0.1 | 0.02 | 4 |
| EXAMPLE 3 | A | 0.2 | 0.04 | 3 |
| EXAMPLE 4 | A | 1.0 | 0.21 | 2 |
| EXAMPLE 5 | A | 4.6 | 1.0 | 7 |
| EXAMPLE 6 | A | 9.2 | 2.0 | 10 |
| EXAMPLE 7 | B | 1.0 | 0.11 | 2 |
| EXAMPLE 8 | C | 1.0 | 0.15 | 2 |
| EXAMPLE 9 | D | 1.0 | 0.05 | 3 |
| EXAMPLE 10 | E | 1.4 | 1.0 | 5 |
| COMPARATIVE EXAMPLE 1 | A | 0.05 | 0.01 | 15 |
| COMPARATIVE EXAMPLE 2 | E | 0.15 | 0.01 | 13 |
| COMPARATIVE EXAMPLE 3 | A | 10.0 | 2.2 | 12 |

Referring to the experimental results of Table 2 according to the first embodiment of the present invention, while the measurement error is less than or equal to ±10% in Example 1 through Example 10, the measurement error exceeds ±10% in Comparative Example 1 through Comparative Example 3.

As is seen from the experimental results of Table 2, the flow rate of exhaust gas is caused to vary using the cells of Samples A through E as the cell 42b in the experiment of FIG. 6 according to the first embodiment of the present invention.

Table 2 shows that the measurement error can be less than or equal to ±10% in any example if the flow rate of exhaust gas passing through the cell wall is within the range of 0.02 m/s to 2.0 m/s. Particularly, within the flow rate range of 0.11 m/s to 0.21 m/s, the measurement error can be less than or equal to ±2% even if the intake flow rate varies from 0.6 l/min. to 1.0 l/min.

Further, according to this embodiment, the measurement error of the particulate matter concentration measuring apparatus 40PM is minimized by controlling the flow velocity of exhaust gas passing through the cell wall of the cell 42b. This velocity Vs of exhaust gas passing through the cell wall may be controlled by controlling the flow rate of exhaust gas "Q2." Such control of the flow rate of exhaust gas "Q2" may also be performed by detecting the flow rate of exhaust gas "Q2" in the exhaust gas extraction line 41A with the flow rate measuring part 44 and controlling the flow rate control valve 43.

The shape parameters "α," "b," "c," "e," "L1cell", and "Ws" illustrated in FIGS. 7A and 7B and the porosity "p" may be determined as desired by selecting the molding and the firing conditions of ceramic in manufacturing the cell 42b.

Figure 9:
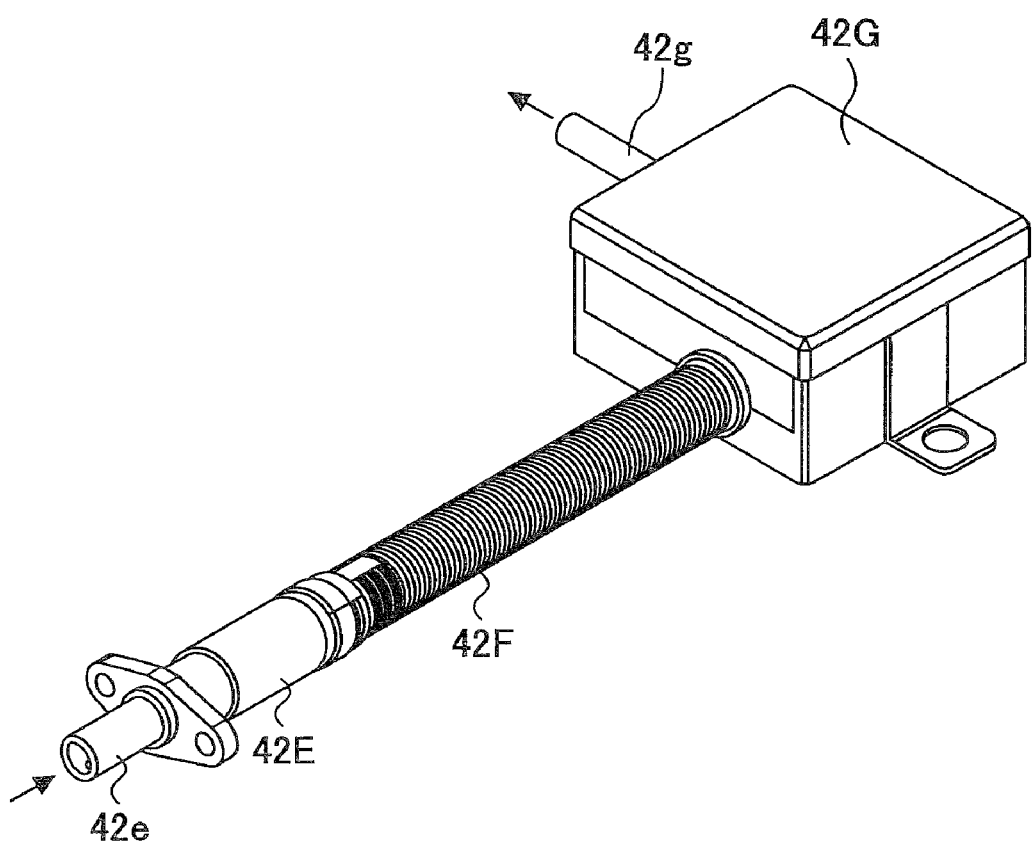
FIG. 9 is a diagram illustrating the particulate matter concentration measuring apparatus according to the first embodiment of the present invention.

The particulate matter concentration measuring apparatus 40PM of this embodiment illustrated in FIG. 9 includes the pipe-shaped housing 42E of a refractory metal such as stainless steel, in which a head part 42e inserted into and fixed to the exhaust line 21 illustrated in FIG. 2 on the downstream side of the diesel particulate filter 22 is formed. The particulate matter detection filter 42A, formed preferably of porous ceramic such as SiC, is provided in the housing 42E. The head part 42e forms the exhaust gas extraction line 41A inserted into the exhaust line 21.

As illustrated in FIG. 9, according to this embodiment, a flexible hose 42F through which exhaust gas passes extends from the housing 42E, and a control unit 42G that houses the differential pressure measuring part 42B, the flow rate control valve 43, and the flow rate measuring part 44 is formed at the downstream end of the flexible hose 42F. The exhaust gas that has passed through the control unit 42G is discharged into an exhaust pipe 42g.

This configuration allows a desired particulate matter concentration measuring apparatus to be reduced in size, thus enabling the particulate matter concentration measuring part to be attached to any part of a vehicle as required.

Figure 10:
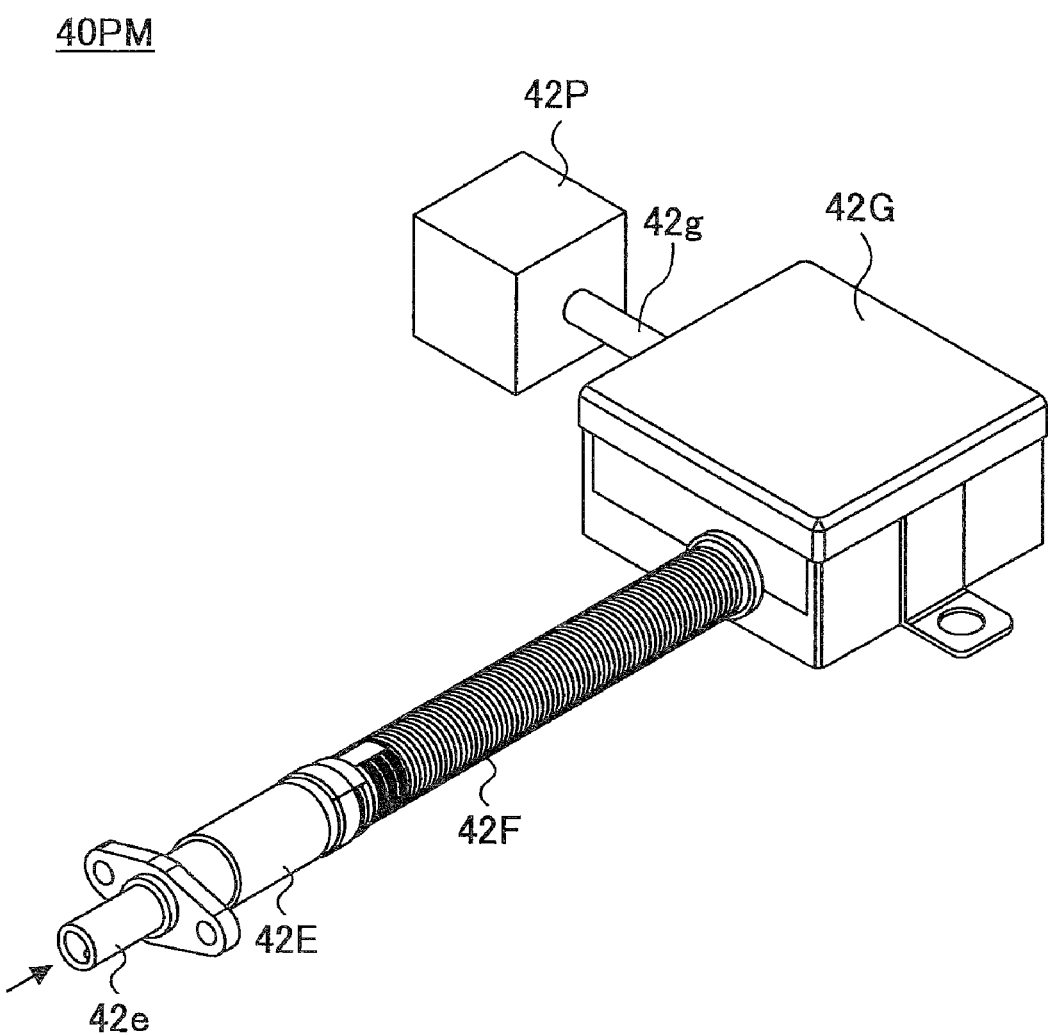
FIG. 10 is a diagram illustrating a variation of the particulate matter concentration measuring apparatus according to the first embodiment of the present invention.

According to a variation of this embodiment, as illustrated in FIG. 10, a pump 42P may be connected to the exhaust pipe 42g for discharging exhaust gas from the control unit 42G in the configuration of this embodiment of FIG. 9 so as to force the discharging of the exhaust gas. According to this configuration, even if the head part 42e is provided in a stationary exhaust gas atmosphere, that is, an exhaust gas atmosphere without flow, the exhaust gas is suctioned in by the negative pressure generated by the pump 42P, thus making it possible to measure particulate matter concentration as desired.

Second Embodiment

Figure 11:
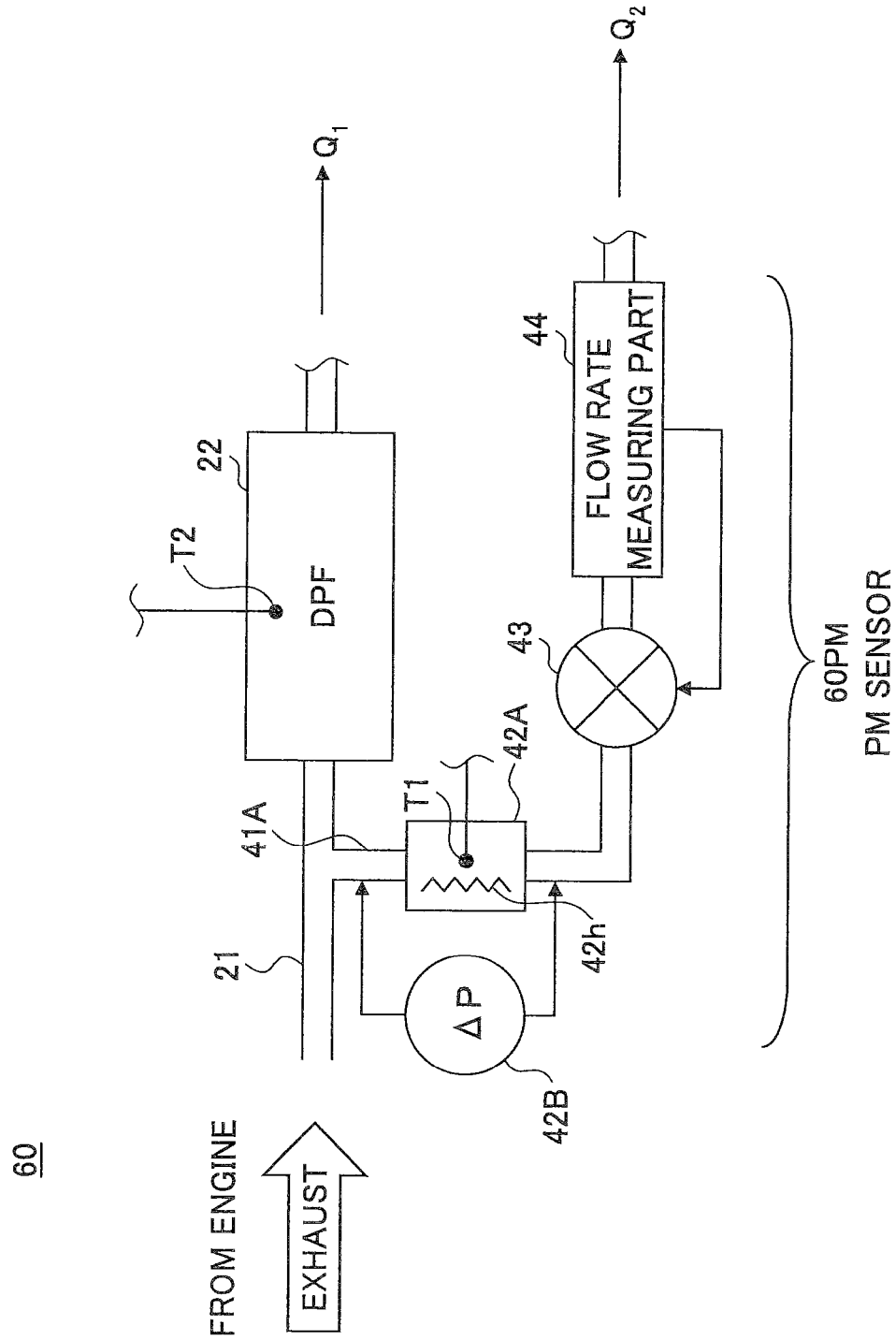
FIG. 11 is a diagram illustrating an exhaust gas purifying apparatus using a particulate matter concentration measuring apparatus according to a second embodiment of the present invention.

FIG. 11 illustrates an exhaust gas purifying apparatus 60 for a diesel engine having a particulate matter concentration apparatus 60PM (PM sensor) according to a second embodiment of the present invention.

Referring to FIG. 11, according to the second embodiment of the present invention, the exhaust gas purifying apparatus 60, which is similar in configuration to the exhaust gas purifying apparatus 20 of FIG. 1, includes the exhaust gas extraction line 41A diverging from the exhaust line 21 on the upstream side of the diesel particulate filter (DPF) 22.

According to the configuration of the second embodiment of the present invention illustrated in FIG. 11, exhaust gas that has not passed through the diesel particulate filter 22 is trapped in the particulate matter detection filter 42A, and the following operation is performed in addition to Eq. (1) through Eq. (3) described above based on the amount of the particulate matter trapped in the particulate matter detection filter 42A.

The concentration of particulate matter in the exhaust gas, "PMconc," is the same in the exhaust gas extraction line 41A and in the exhaust line 21. Accordingly, the amount of particulate matter passing through the exhaust line 21 ("PMenter full filter" [g/h]) is determined by:

$$\text{PMenter full filter [g/h]} = \text{PMconc [g/m}^3\text{]} \times Q1, \quad (4)$$

where "Q1" represents the flow rate of exhaust gas in the exhaust line 21.

Thereby, it is possible to estimate the amount of particulate matter accumulated in the diesel particulate filter (DPF) 22. "Q1" is the flow rate of exhaust gas passing through the diesel particulate filter (DPF) 22. "Q1" may be determined by actual measurement or be estimated from the operating condition of the engine.

In the configuration of the second embodiment of the present invention illustrated in FIG. 11, the flow rate control valve 43 is provided in the exhaust gas extraction line 41A. Like in the case of the exhaust gas purifying apparatus 20 of FIG. 1, the flow rate control valve 43 is controlled by the flow rate measuring part 44 so that the flow rate of exhaust gas in the exhaust gas extraction line 41 is controlled to a predetermined value "Q2."

On the other hand, according to such a configuration, particulate matter is deposited in the particulate matter detection filter 42A over time. Accordingly, the particulate matter detection filter 42A is regenerated.

Therefore, according to this embodiment, a heater 42h is formed on the particulate matter detection filter 42A (cell 42b). The heater 42h is driven as required with power from a driving line, thereby combusting the particulate matter primarily of C (carbon) trapped by the cell 42b to regenerate the particulate matter detection filter 42A.

It is possible to produce the same effects as in the first embodiment also in this embodiment.

According to an embodiment of the present invention, the flow velocity of exhaust gas passing through the cell wall of the particulate matter detection filter 42A is optimized to prevent uneven deposition of particulate matter on the particulate matter detection filter 42A, so that the accuracy of detecting the amount of particulate matter in the exhaust gas increases.

The present invention is not limited to the specifically disclosed embodiments, and variations and modifications may be made without departing from the scope of the present invention.

For example, the flow rate measuring part 44 in the above-described embodiments may be omitted if the flow rate of exhaust gas flowing through the exhaust gas extraction line 41A is known in advance. Further, the temperature measuring part T1 may be omitted if the exhaust gas is considered as constant in characteristics. Furthermore, the heater 42h in the second embodiment of the present invention may be omitted if there is no need for regeneration. Moreover, the flow rate control valve 43 may be omitted if the flow rate is measured with accuracy. Further, the heater 42h described in the second embodiment of the present invention may also be provided in the particulate matter concentration measuring apparatus 40PM of the first embodiment of the present invention.

The flow rate control valve 43 and the pump 42P (see FIG. 10) may be used together. Further, it is also possible to structurally control the flow rate of the exhaust gas caused to flow into the exhaust gas extraction line 41A by combining the cross-sectional area of the exhaust gas extraction line 41A and the volume of the particulate matter detection filter 42A.

What is claimed is:

1. A particulate matter concentration measuring apparatus configured to measure a concentration of particulate matter in exhaust gas flowing through an exhaust line of a diesel engine, the apparatus comprising:
   an exhaust gas extraction line diverging from the exhaust line and having a flow passage cross-sectional area smaller than a flow passage cross-sectional area of the exhaust line;
   a particulate matter detection filter having a cell wall and provided in the exhaust gas extraction line, a flow velocity of the exhaust gas passing through the cell wall being more than or equal to approximately 0.02 m/s and less than or equal to approximately 2.0 m/s; and
   a differential pressure sensing part configured to sense a differential pressure generated between an inlet and an outlet of the particulate matter detection filter.

2. The particulate matter concentration measuring apparatus as claimed in claim 1, wherein the flow velocity of the exhaust gas passing through the cell wall of the particulate matter detection filter is more than or equal to approximately 0.11 m/s and less than or equal to approximately 0.21 m/s.

3. The particulate matter concentration measuring apparatus as claimed in claim 1, further comprising:
   a flow velocity controller configured to control the flow velocity of the exhaust gas passing through the particulate matter detection filter.

4. The particulate matter concentration measuring apparatus as claimed in claim 3, wherein the flow velocity controller comprises:
   a flow rate measuring part inserted into the exhaust gas extraction line and configured to measure a flow rate of the exhaust gas in the exhaust gas extraction line;
   a flow rate control valve inserted into the exhaust gas extraction line and configured to control the flow rate of the exhaust gas in the exhaust gas extraction line; and
   a control part configured to control the flow rate control valve based on the flow rate of the exhaust gas measured in the flow rate measuring part so that the flow rate of the exhaust gas in the exhaust gas extraction line is controlled to a predetermined value.

5. The particulate matter concentration measuring apparatus as claimed in claim 3, wherein the flow velocity controller comprises a pump provided on a downstream side of the particulate matter detection filter.

6. The particulate matter concentration measuring apparatus as claimed in claim 1, further comprising:
   a diesel particulate filter provided in the exhaust line, the diesel particulate filter having a filter volume greater than a filter volume of the particulate matter detection filter.

7. The particulate matter concentration measuring apparatus as claimed in claim 6, wherein the exhaust gas extraction line is connected to the exhaust line on a downstream side of the diesel particulate filter.

8. The particulate matter concentration measuring apparatus as claimed in claim 6, wherein the exhaust gas extraction line is connected to the exhaust line on an upstream side of the diesel particulate filter.

9. The particulate matter concentration measuring apparatus as claimed in claim 1, further comprising:
   a negative pressure part provided on a downstream side of the particulate matter detection filter.

* * * * *